US010201652B2

(12) United States Patent
Dutra et al.

(10) Patent No.: US 10,201,652 B2
(45) Date of Patent: *Feb. 12, 2019

(54) ACOUSTOPHORETIC SEPARATION OF LIPID PARTICLES FROM RED BLOOD CELLS

(71) Applicant: FloDesign Sonics Inc., Wilbraham, MA (US)

(72) Inventors: Brian Dutra, Rockland, MA (US); Bart Lipkens, Hampden, MA (US); Daniel Kennedy, Longmeadow, MA (US); Michael J. Rust, Springfield, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 193 days.

This patent is subject to a terminal disclaimer.

(21) Appl. No.: 13/866,584

(22) Filed: Apr. 19, 2013

(65) Prior Publication Data

US 2013/0277316 A1 Oct. 24, 2013

Related U.S. Application Data

(60) Provisional application No. 61/636,515, filed on Apr. 20, 2012.

(51) Int. Cl.
*C02F 1/36* (2006.01)
*H04R 23/00* (2006.01)
(Continued)

(52) U.S. Cl.
CPC .......... *A61M 1/3681* (2013.01); *A61M 1/363* (2014.02); *A61M 1/3678* (2014.02); *B01D 21/283* (2013.01); *A61M 2202/08* (2013.01)

(58) Field of Classification Search
CPC combination set(s) only.
See application file for complete search history.

(56) References Cited

U.S. PATENT DOCUMENTS 4,800,316 A * 1/1989 Ju-Zhen ............... G10K 11/002
252/515
5,527,460 A * 6/1996 Trampler ............. B01D 21/283
209/155

(Continued)

FOREIGN PATENT DOCUMENTS

WO WO 02/072234 A1 9/2002
WO WO 2010040394 A1 * 4/2010 ........... B01D 21/283
(Continued)

OTHER PUBLICATIONS

Lipkens, B., et al. "Separation of bacterial spores from flowing water in macro-scale cavities by ultrasonic standing waves", submitted/uploaded to http://arxiv.org/abs/1006.5467 on Jun. 28, 2010.*
(Continued)

*Primary Examiner* — Krishnan S Menon
*Assistant Examiner* — Ryan Huang
(74) *Attorney, Agent, or Firm* — Rick Klein, Esq; Fay Sharpe, LLP

(57) ABSTRACT

A system for removing lipids from blood during cardiopulmonary bypass surgery is disclosed. The system uses an acoustophoretic separator having improved trapping force. The transducer of the acoustophoretic seperator includes a ceramic crystal. Blood flows through the separator, and lipids are trapped and removed.

15 Claims, 14 Drawing Sheets

(51) Int. Cl.
*A61M 1/36* (2006.01)
*B01D 21/28* (2006.01)

(56) References Cited

U.S. PATENT DOCUMENTS

| | | | | |
|---|---|---|---|---|
| 6,332,541 | B1* | 12/2001 | Coakley | B01J 19/10 209/160 |
| 6,475,151 | B2* | 11/2002 | Koger | B06B 1/0674 600/459 |
| 6,881,314 | B1* | 4/2005 | Wang et al. | 204/600 |
| 2001/0031922 | A1* | 10/2001 | Weng | A61B 17/0057 600/439 |
| 2006/0037915 | A1* | 2/2006 | Strand | B01D 21/283 210/748.05 |
| 2008/0245709 | A1* | 10/2008 | Kaduchak et al. | 209/599 |
| 2008/0316866 | A1* | 12/2008 | Goodemote | G10K 11/008 367/151 |
| 2011/0125024 | A1* | 5/2011 | Mueller | G10K 11/002 600/459 |
| 2011/0154890 | A1* | 6/2011 | Holm | B01D 21/283 73/61.75 |
| 2012/0163126 | A1* | 6/2012 | Campbell | B06B 1/0614 367/135 |
| 2013/0175226 | A1* | 7/2013 | Coussios et al. | 210/748.05 |

FOREIGN PATENT DOCUMENTS

| | | |
|---|---|---|
| WO | WO 2011/027146 A2 | 3/2011 |
| WO | WO 2011/161463 A2 | 12/2011 |
| WO | WO 2011161463 A2 * | 12/2011 |

OTHER PUBLICATIONS

International Search Report and Written Opinion of International Application No. PCT/US2013/037404 dated Jun. 21, 2013.
Kuznetsova Larisa A, et al., "Microparticle concentration in short path length ultrasonic resonators: Roles of radiation pressure and acoustic streaming", J. Acoust. Soc. Am. 116 (4), Pt. 1, Oct. 2004, pp. 1956-1966.

* cited by examiner

ACOUSTOPHORETIC SEPARATION OF LIPID PARTICLES FROM RED BLOOD CELLS

This application claims priority to U.S. Provisional Patent Ser. No. 61/636,515, filed Apr. 20, 2012. The entirety of this application is hereby incorporated by reference in its entirety.

BACKGROUND

During cardiac surgery, the function of the heart and lungs is replaced by an external pump due to the difficulty of operating on a beating heart. This technique, called cardiopulmonary bypass (CPB), maintains circulation of blood and oxygen in the patient's body. Retransfusion is attractive because it reduces the need for allogeneic transfusion, minimizes costs, and decreases transfusion-related morbidity. Heterologous transfusions are also linked to increased long term mortality after cardiac surgery.

However, when layers of fat are cut during surgery, they release lipids that can be collected by the pump during suctioning. These lipids are then unintentionally introduced to the bloodstream when blood is re-transfused to the body. The lipids can cause lipid microemboli, in which the emulsified (in suspension) fat cells travel to the patient's organs (e.g. kidney, lung, heart) and can cause blockage of blood vessels (embolization). This is especially dangerous when lipid micro-emboli occur in the brain, as they can cause various neuro-cognitive disorders. More than 50% of patients experience neurological deficits in the first week after CPB, 10-30% have long term or permanent affects, and 1-5% experience permanent disability or death.

Existing methods for removing lipids from blood, such as filtering and centrifugation, are either inefficient or harmful to the beneficial red blood cells in the flood. Lipid particles show a size distribution of approximately 5-70 micrometers (μm) in diameter, with most particles being ≤10 μm. This is about the same size as red blood cells. Typical filters have a pore size of 25-40 μm, and a lipid removal efficiency of 30-40%. Also, filters clog and suffer from throughput constraints, need replacement, and may disperse larger droplets into smaller droplets. Centrifugation is time-consuming, expensive, and requires trained personnel. Also, the high speeds required for centrifugation may damage the blood cells, and removes beneficial blood components such as platelets and clotting factors. Some MEMS devices have been used, but rely on very small passages that essentially "line up" red blood cells and lipid particles for separation. This results in very low throughput, and cannot handle large amounts in bulk.

There is a need for a separation technology that can efficiently and adequately remove lipids from blood.

BRIEF DESCRIPTION

The present disclosure relates to systems and devices that use acoustophoresis to trap and separate lipids from blood. The devices use an ultrasonic transducer as described herein.

Method of separating lipids from blood are disclosed herein. The blood is flowed through a flow chamber. The flow chamber has a source of acoustic energy and, on an opposing side of the flow chamber, a reflector of acoustic energy. The blood contains lipids. The source of acoustic energy is activated to create a plurality of incident waves in the blood. The reflector reflects the plurality of incident waves, creating a plurality of reflected waves resonating with the incident waves, thus forming a plurality of standing waves. Lipids trapped in the standing waves can then be removed from the blood.

In other embodiments, an apparatus is disclosed. The apparatus includes a flow chamber with an inlet and an outlet through which is flowed blood containing lipids, an ultrasonic transducer on a wall of the flow chamber, the transducer including a ceramic crystal that defines a side of the transducer, the transducer being driven by an oscillating, periodic, or pulsed voltage signal of ultrasonic frequencies which drives the transducer to create standing waves in the flow chamber, and a reflector located on a wall on the opposite side of the flow chamber from the transducer.

In yet another embodiment, an apparatus comprises a suction to gather blood from a patient, a flow chamber with an inlet and an outlet through which is flowed the blood, a plurality of ultrasonic transducers located on a wall of the flow chamber, the transducers each including a ceramic crystal driven by an oscillating, periodic, or pulsed voltage signal of ultrasonic frequencies which drives the transducers to vibrate in a non-uniform mode of displacement to create standing waves in the flow channel, and a reflector located on the wall on the opposite side of the flow chamber from the transducers.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
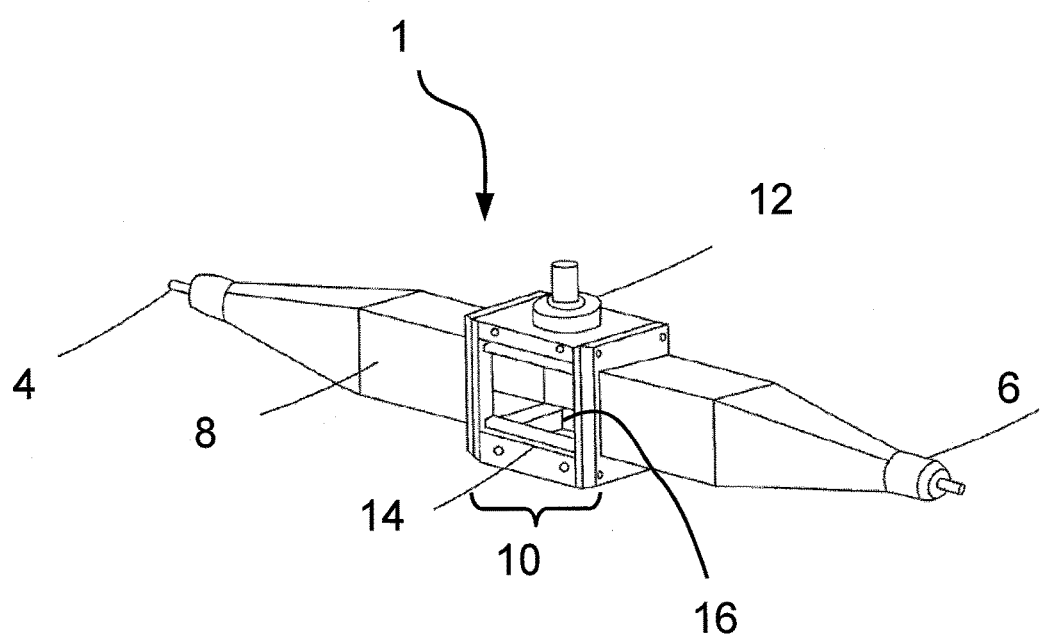
FIG. 1 shows an acoustophoretic separator having one transducer.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of."

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4."

Some of the terms used herein are relative terms. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. The terms "upper" and "lower" are relative to a central point. An upper component is located in one direction from the central point and a lower component would be located in the opposite direction from the central point.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The present disclosure refers to particles and droplets. "Particles" should be considered to refer to materials that are denser than water, while "droplets" refers to materials that are less dense than water. However, these two terms also share a common characteristic of being suspended or dispersed in fluid, and are desirably separated from the fluid. Depending on the context, reference to any one of the terms should be construed as referring to either term due to this common characteristic, and thus should not be construed as somehow being limited to only the one used term based on density.

As previously mentioned, efficient separation technologies for multi-component liquid streams, such as lipids from blood, are needed. In this regard, the term "blood" refers to the combination of blood cells suspended in plasma. The term "plasma" refers to the liquid component of blood that contains dissolved proteins, glucose, clotting factors, mineral ions, hormones and carbon dioxide. The term "blood cells" refers to both red blood cells and white blood cells. Lipids, which are desirably removed from the blood, are about the same size as blood cells, which makes separation using conventional methods difficult.

Acoustophoresis

Acoustophoresis is the separation of particles using high intensity sound waves. It has long been known that high intensity standing waves of sound can exert forces on particles. A standing wave has a pressure profile which appears to "stand" still in time. The pressure profile in a standing wave varies from areas of high pressure (nodes) to areas of low pressure (anti-nodes). Standing waves are produced in acoustic resonators. Common examples of acoustic resonators include many musical wind instruments such as organ pipes, flutes, clarinets, and horns.

Acoustophoresis is a low-power, no-pressure-drop, no-clog, solid-state approach to particle removal from fluid dispersions: i.e., it is used to achieve separations that are more typically performed with porous filters, but it has none of the disadvantages of filters.

Acoustophoretic phase separator technology using ultrasonic standing waves provides the benefit of having no consumables, no generated waste, and a low cost of energy. The technology is efficient at removal of particles of greatly varying sizes, including separation of micron and sub-micron sized particles, as explained in commonly owned U.S. patent application Ser. No. 13/844,754, which is hereby incorporated by reference in its entirety. Examples of acoustic filters/collectors utilizing acoustophoresis can be found in commonly owned U.S. patent application Ser. Nos. 12/947, 757; 13/085,299; 13/216,049; and 13/216,035, the entire contents of each being hereby fully incorporated by reference.

Acoustophoresis can be used to separate the similarly sized blood cells and lipids from each other, so that only the lipids are removed. Acoustophoresis can be used in a continuous flow process, in which the blood flows through a flow chamber, allowing a continuous loop process without any flow interruption. In the flow chamber, the lipids are separated from the blood cells and the plasma, and can thus be removed. This can be useful for example during surgery, when lipids are introduced into the bloodstream of a surgery patient. The lipids can be removed from the bloodstream during the external circulation loop of the blood, reducing the likelihood of lipid micro-emboli due to the surgery. This can reduce post-surgery complications. The macro-scale device permits flow rates up to several liters per hour (L/hr). No specially trained personnel is needed.

The acoustic resonator is designed to create a high intensity three dimensional ultrasonic standing wave that results in an acoustic radiation force that is larger than the combined effects of fluid drag and buoyancy, and is therefore able to trap, i.e., hold stationary, the suspended phase. The present systems have the ability to create ultrasonic standing wave fields that can trap particles in flow fields with linear velocity exceeding 1 cm/s. Excellent particle separation efficiencies have been demonstrated for particle sizes as small as one micron—much smaller than the blood and lipid cells.

The acoustophoretic separation technology employs ultrasonic standing waves to trap, i.e., hold stationary, secondary phase particles in a host fluid stream. This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius). It is proportional to frequency and the acoustic contrast factor. It also scales with acoustic energy (e.g. the square of the acoustic pressure amplitude). The sinusoidal spatial variation of the force is what drives the particles to the stable positions of the standing waves. When the acoustic radiation force exerted on the particles is stronger than the combined effect of fluid drag force and buoyancy/gravitational force, the particle is trapped within the acoustic standing wave field. The action of the acoustic forces on the trapped particles results in concentration, agglomeration and/or coalescence of particles and droplets. Heavier-than-water (i.e. denser than water, such as red blood cells) particles are separated through enhanced gravitational settling, and lighter-than-water particles (e.g. lipids) are separated through enhanced buoyancy.

A schematic representation of one embodiment of an acoustophoretic particle separator 1 is shown in FIG. 1. A multi-component liquid stream (e.g. water or other fluid) enters the inlet 4 and separated fluid exits at the opposite end via outlet 6. It should be noted that this liquid stream is usually under pressure when flowing through the separator. The particle separator 1 has a longitudinal flow channel 8 that carries the multi-component liquid stream and passes through a resonator 10. The resonator 10 includes a transducer 12 or, in some embodiments, an array of transducers, which acts as an excitation source of acoustic waves. The acoustic resonator 10 has a reflector 14, which is located on the wall opposite the transducer 12. A collection pocket 16 collects impurities, and is also located opposite the transducer. As defined herein, impurities includes particles or fluids distinct from the host fluid. Another collection pocket (not visible) is located at the top of the device near the transducer. The acoustic resonator 10 is designed to maintain a high intensity three-dimensional acoustic standing wave. The system is driven by a function generator and amplifier (not shown). The system performance is monitored and controlled by a computer.

Figure 2:
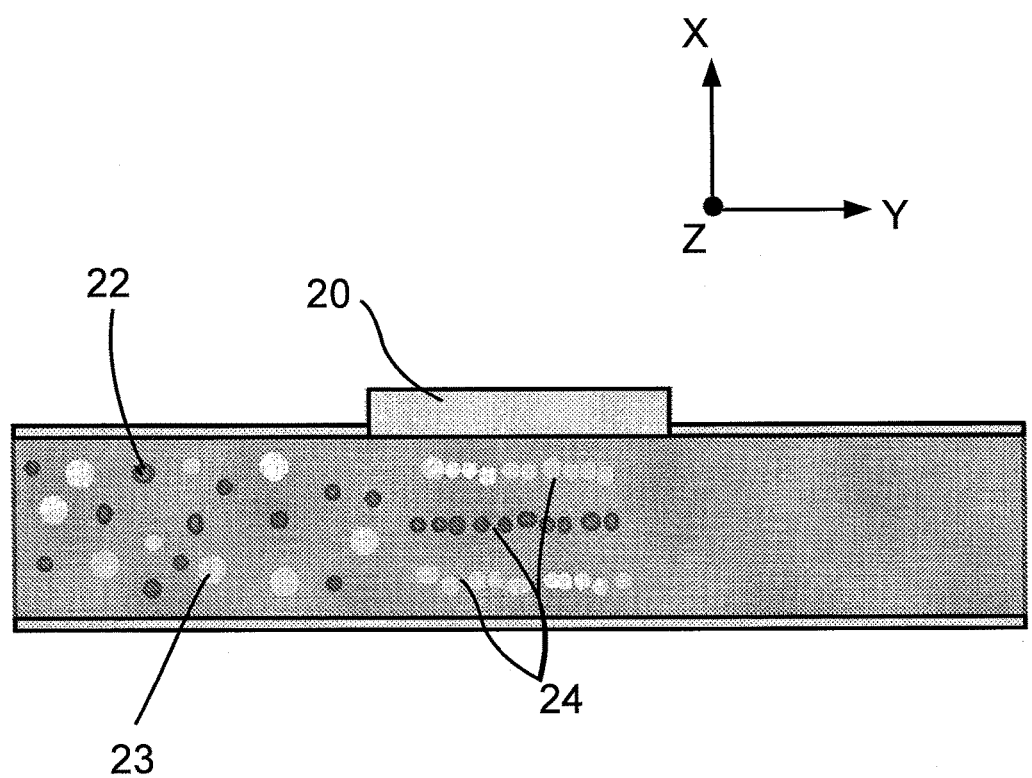
FIG. 2 is a diagram illustrating the function of an acoustophoretic separator.

A diagrammatic representation of an embodiment for removing lipids from blood is shown in FIG. 2. Excitation frequencies typically in the range from hundreds of kHz to several MHz are applied by transducer 20. Blood cells 22 and lipids 23 are trapped at the nodes of standing waves 24 and agglomerate, allowing the buoyant lipids to float to the top and the heavier blood cells to sink. The acoustophoretic separation technology can accomplish multi-component particle separation without any fouling at a much reduced cost.

Figure 3:
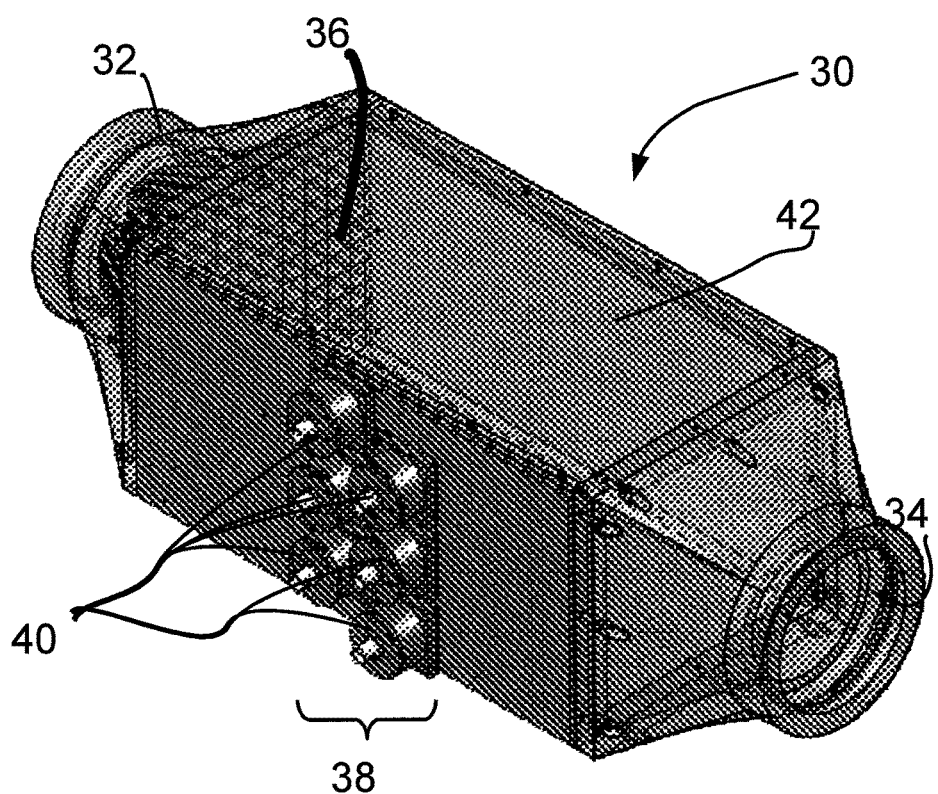
FIG. 3 shows an acoustophoretic separator having a plurality of transducers.

FIG. 3 shows another embodiment of an acoustophoretic particle separator 30. Like acoustophoretic separator 1, acoustophoretic separator 30 has a housing 42 with an inlet 32 and an outlet 34. The inlet 32 is fitted with a nozzle or diffuser 36 having a honeycomb to facilitate the development of plug flow. The acoustophoretic separator 30 has an array 38 of transducers 40, in this case six transducers all arranged on the same wall. The transducers are arranged so that they cover the entire cross-section of the flowpath. The acoustophoretic separation system of FIG. 3 has, in certain embodiments, a square cross section of 6 inches×6 inches which operates at flow rates of up to 3 gallons per minute (GPM), or a linear velocity of 8 mm/sec. The transducers 40 are six PZT-8 (Lead Zirconate Titanate) transducers with a 1 inch diameter and a nominal 2 MHz resonance frequency. Each transducer consumes about 28 W of power for droplet trapping at a flow rate of 3 GPM. This translates in an energy cost of 0.25 kW hr/m$^3$. This is an indication of the very low cost of energy of this technology. Desirably, each transducer is powered and controlled by its own amplifier.

Figures 4A, 4B:
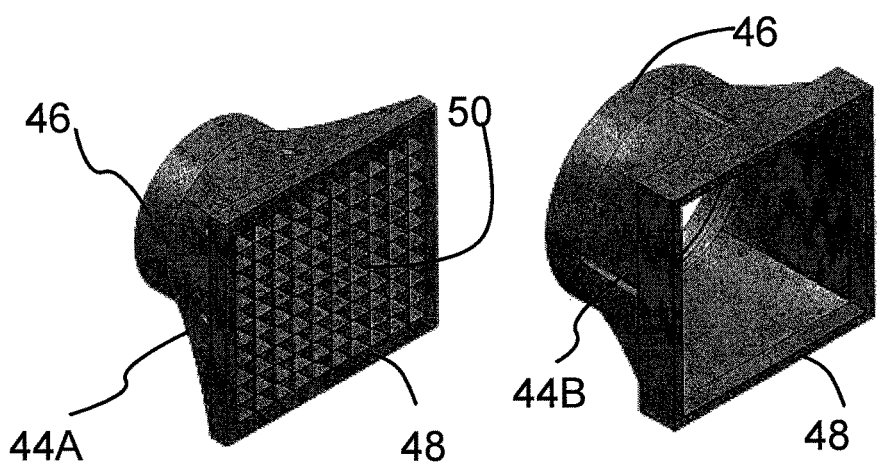
FIG. 4A is a detail view of a diffuser used as an inlet in the separator of FIG. 3.
FIG. 4B is a detail view of an alternate inlet diffuser that can be used with the separator of FIG. 3.

FIG. 4A and FIG. 4B show two different diffusers that can be used at the inlet of the acoustophoretic separator. The diffusers 44A and 44B have an entrance 46 (here with a circular shape) and an exit 48 (here with a square shape). The diffuser of FIG. 4A is illustrated in FIG. 3. FIG. 4A includes a grid or honeycomb 50, whereas FIG. 4B does not. The grid helps ensure uniform flow.

Figure 5:
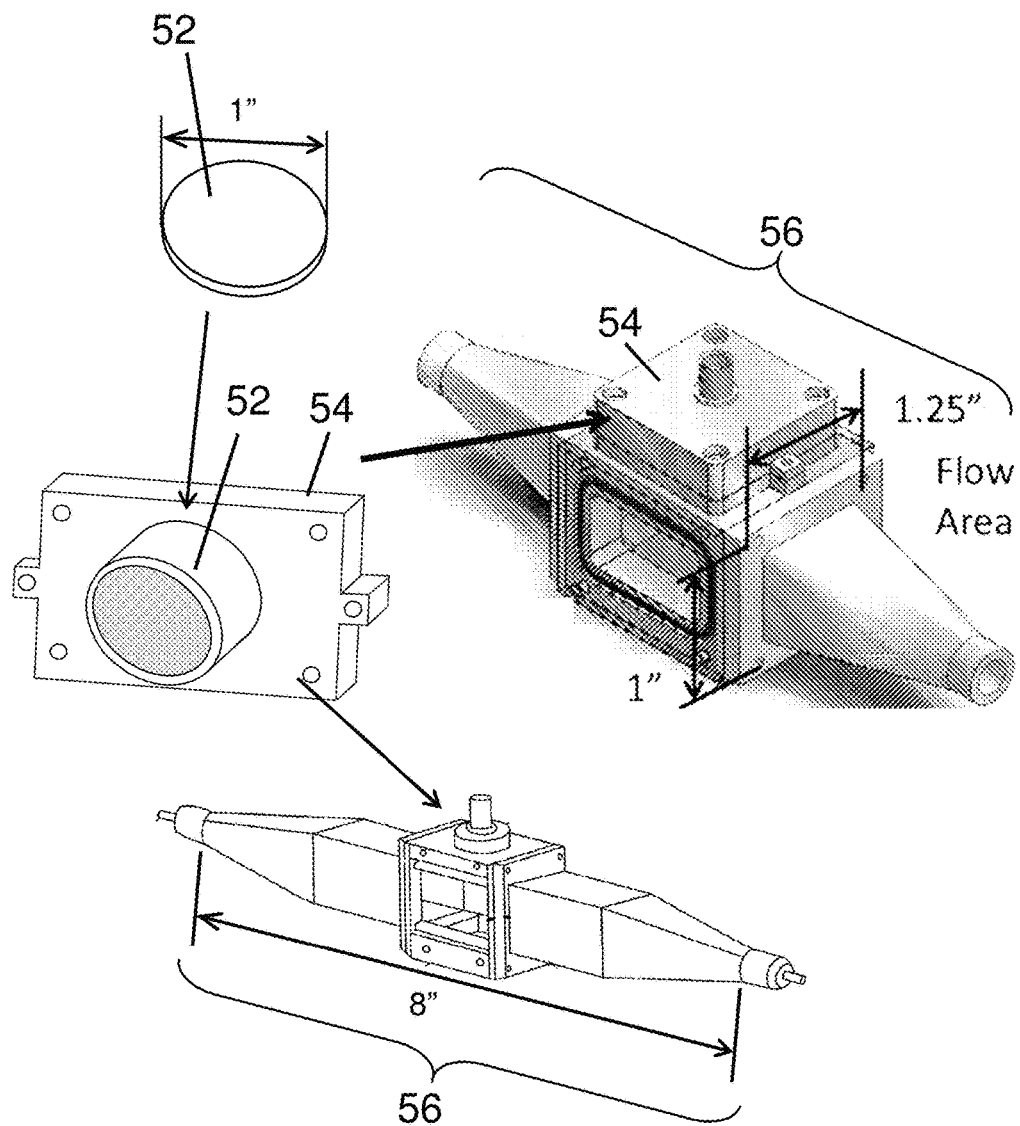
FIG. 5 is an alternative embodiment of an acoustophoretic separator having one transducer.

FIG. 5 is another embodiment of an acoustophoretic separator having one transducer. The transducer 54 has a PZT-8 piezoelectric crystal 52. The transducer 54 is mounted to the top of the separator 56.

Figure 6:
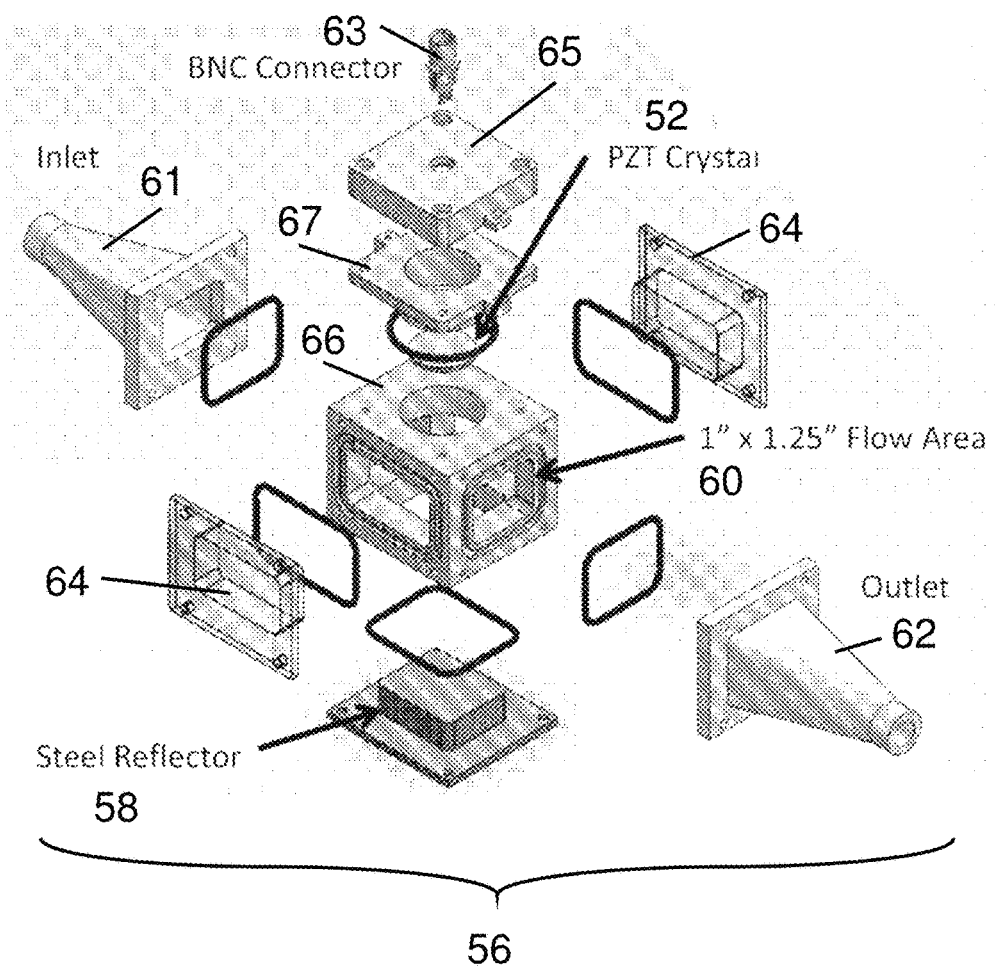
FIG. 6 is an exploded view of the acoustophoretic separator of FIG. 5.

FIG. 6 is an exploded view of the separator of FIG. 5, showing the separate components. At the center of the separator is a body 66 that is illustrated here as having six faces surrounding a chamber 60. Put another way, the body is hollow. The chamber 60 is where the standing waves are produced and where the separation of blood and lipids occurs. Here, each face includes a hole to access the chamber. An inlet 61 and an outlet 62 are located here on opposite faces of the body. In use, blood enters the separator through the inlet 61 and exits through the outlet 62. Shown here on the top face is a circular hole through which the ultrasonic transducer is exposed to the blood. Circular crystal 52 is shown here. Also located on the top face is a transducer support piece 67 and a top piece 65. It is contemplated that the ultrasonic transducer will be placed into the support piece 67 and then covered by the top piece 65. Not shown here, but contemplated, is a collection pocket at the top into which the separated lipids can be directed. A hole in the top piece permits a BNC connector 63 to be connected to the transducer. On the bottom face (i.e. opposite the transducer) is a reflector plate 58, here made out of steel. Viewing windows 64 are placed in the two remaining faces. These viewing windows are optional. Gaskets are present around each hole of the body, to enhance watertightness.

Figure 7:
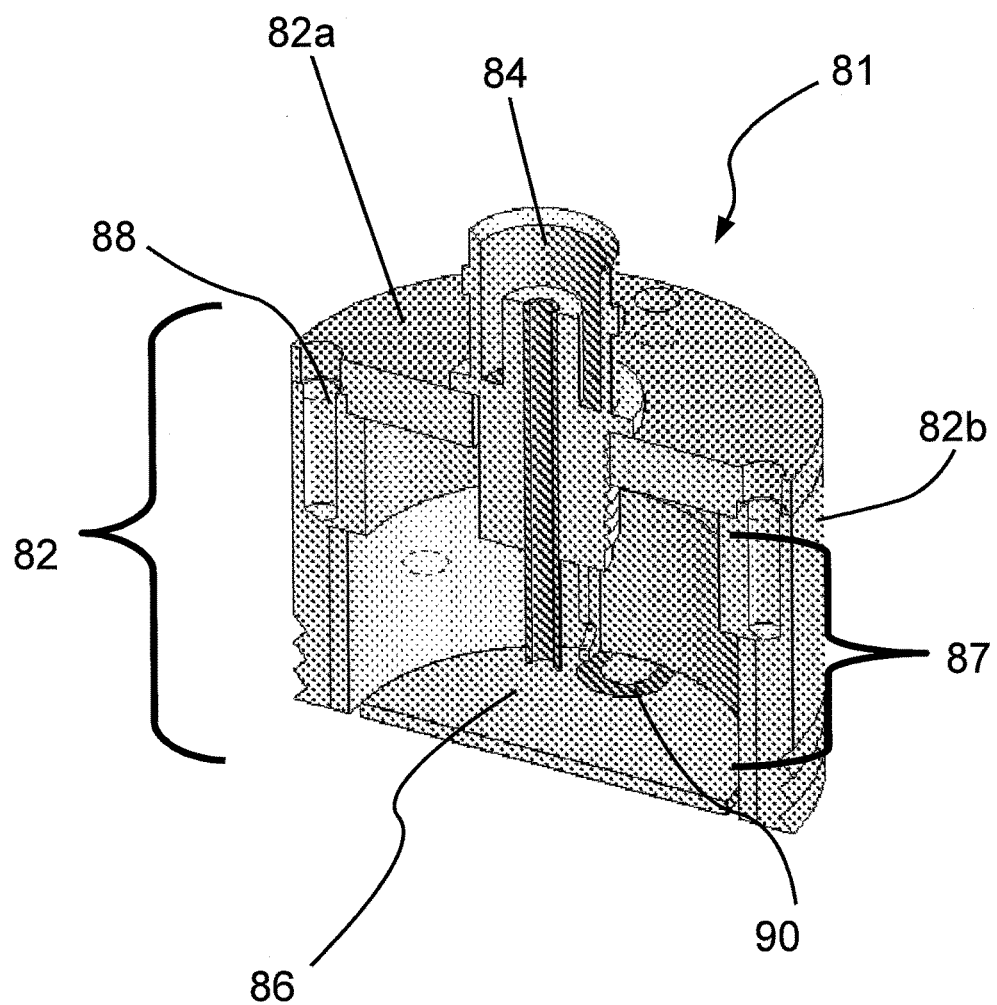
FIG. 7 is a cross-sectional diagram of an ultrasonic transducer of the present disclosure. An air gap is present within the transducer, and no backing layer is present.

FIG. 7 is a cross-sectional view of an ultrasonic transducer 81 of the present disclosure, which can be used with the acoustophoretic separators of FIG. 1, FIG. 3, or FIG. 5. The transducer 81 would be located in the transducer support piece 67 of FIG. 6.

The transducer 81 has an aluminum housing 82. A PZT crystal 86 defines the bottom end of the transducer, and is exposed from the exterior of the housing. The crystal is supported on its perimeter by the housing.

Screws (not shown) attach an aluminum top plate 82a of the housing to the body 82b of the housing via threads 88. The top plate includes a connector 84 to pass power to the PZT crystal 86 (which interfaces with the BNC connector 63 of FIG. 6). Electrical power is provided to the PZT crystal 86 by electrical lead 90. Note that the crystal 86 has no backing layer. Put another way, there is an air gap 87 in the transducer between aluminum top plate 82a and the crystal 86. A minimal backing may be provided in some embodiments.

The transducer design affects performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half or quarter wavelength thickness, and manufacturing methods may not be appropriate. Rather, in one embodiment of the present disclosure the transducers have no wear plate or backing, allowing the crystal to vibrate with a high Q-factor. In this regard, the Q-factor describes the sound emanating from the transducer according to the equation $Q=f_0/\text{bandwidth}$, where $f_0$ is the center frequency and the bandwidth is the width of the frequency distribution. A "high-Q" transducer has a relatively small bandwidth and long spatial pulse length. A "low-Q" transducer has a relatively large bandwidth and short spatial pulse length.

The vibrating ceramic crystal/disk is directly exposed to the fluid flowing through the flow chamber. In embodiments, there is a silver electrode on either side of the vibrating crystal. Typically, there is a thin metal layer on both sides of the PZT crystal so as to excite the transducer.

Removing the backing (e.g. making the crystal air backed) also permits the ceramic crystal to obtain higher order modes of vibration (e.g. higher order modal displacement). In a transducer having a crystal with a backing, the crystal vibrates with a uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood or cork which allows the crystal to vibrate in a higher order mode shape and maintains a high Q-factor while still providing some mechanical support for the crystal. In another embodiment, the backing may be a lattice work that follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal.

Placing the crystal in direct contact with the fluid (i.e. blood) or providing as thin of a wear plate as possible between the crystal and the fluid also contributes to the high Q-factor by avoiding the dampening and energy absorption effects of the wear plate. In a system to separate lipids from blood, a wear plate is advantageous to prevent the PZT, which contains lead, from contacting the blood. Possible wear layers are chrome, electrolytic nickel, or electroless nickel. Chemical vapor deposition could also be used to apply a layer of poly(p-xylxylene) (e.g. PARYLENE™) or other polymer. Organic and biocompatible coatings such as silicone or polyurethane are also contemplated as a wear surface.

The systems of the present disclosure are operated at a voltage such that the particles are trapped in the ultrasonic standing waves, i.e., remain in a stationary position. The particles (i.e. the lipids and the blood cells) are collected in well-defined trapping lines, separated by half a wavelength. Within each nodal plane, the particles are trapped in the minima of the acoustic radiation potential. The axial component of the acoustic radiation force drives particles with a positive contrast factor to the pressure nodal planes, whereas particles with a negative contrast factor are driven to the pressure anti-nodal planes. The radial or lateral component of the acoustic radiation force is the force that traps the particle. In systems using typical transducers, the radial or lateral component of the acoustic radiation force is typically several orders of magnitude smaller than the axial component of the acoustic radiation force. However, the lateral force in separators 1, 30, and 56 can be significant, on the same order of magnitude as the axial force component, and is sufficient to overcome the fluid drag force at linear velocities of up to 1 cm/s. As discussed above, the lateral force can be increased by driving the transducer in higher order mode shapes, as opposed to a form of vibration where the crystal effectively moves as a piston having a uniform displacement. These higher order modes of vibration are similar to the vibration of a membrane in drum modes such as modes (1,1), (1,2), (2,1), (2,2), (2, 3), or (m, n), where m and n are 1 or greater. The acoustic pressure is proportional to the driving voltage of the transducer. The electrical power is proportional to the square of the voltage.

Contrast Factor

The separation of lipids and blood cells is possible due to their differing acoustic contrast factor. The acoustic contrast factor X of a particle p in a fluid f can be calculated according to the following equation:

$$X = \frac{5\rho_p - 2\rho_f}{2\rho_p + \rho_f} - \frac{\beta_p}{\beta_f}$$

where $\rho_p$ is the particle density, $\beta_p$ is the compressibility of the particle, $\rho_f$ is the fluid density, and $\beta_f$ is the compressibility of the fluid.

The plasma can be considered to have properties similar to water, and the following data is shown in Table 1. The "E" notation refers to 10 to the power of the number following, (e.g. E+2=10"2, or 100).

TABLE 1

| Material | Diameter (μm) | Density (kg/m$^3$) | Compressibility (Pa$^{-1}$) | Acoustic Contrast Factor X | $\rho_p/\rho_{H2O}$ | $\beta_p/\beta_{H2O}$ |
|---|---|---|---|---|---|---|
| Water | | 1000 | 4.55E−10 | N/A | N/A | N/A |
| Red Blood Cells | 6-10 | 1092 | 3.48E−10 | 3.22E−01 | 1.092 | 0.76 |
| Lipids | 10-60 | 921 | 5.17E−10 | −2.19E−01 | 0.921 | 1.14 |

Figure 8:
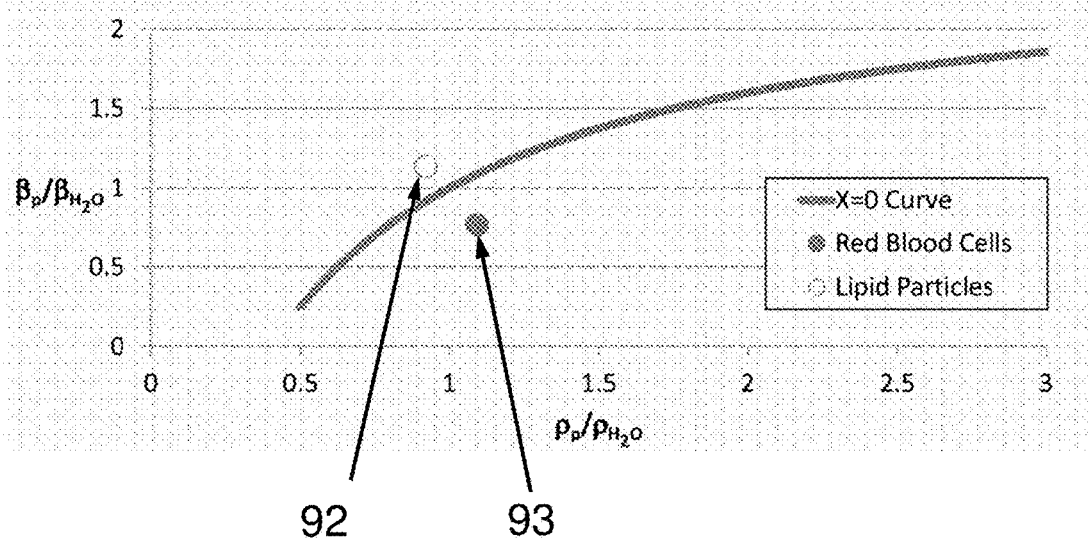
FIG. 8 is a chart showing the contrast factors of blood cells and lipids.

FIG. 8 shows a chart of the acoustic contrast factor (ACF) for red blood cells and lipids with a curve X=0 indicating where the contrast factor is zero, the fluid being water. A particle having a contrast factor of zero would feel no force, having properties similar to the solution it is in (e.g., water). Because the red blood cell contrast factor 93 and the lipid contrast factor 92 are on opposite sides of the X=0 curve, i.e. one has a positive ACF and the other has a negative ACF, they can be efficiently separated.

Figure 9:
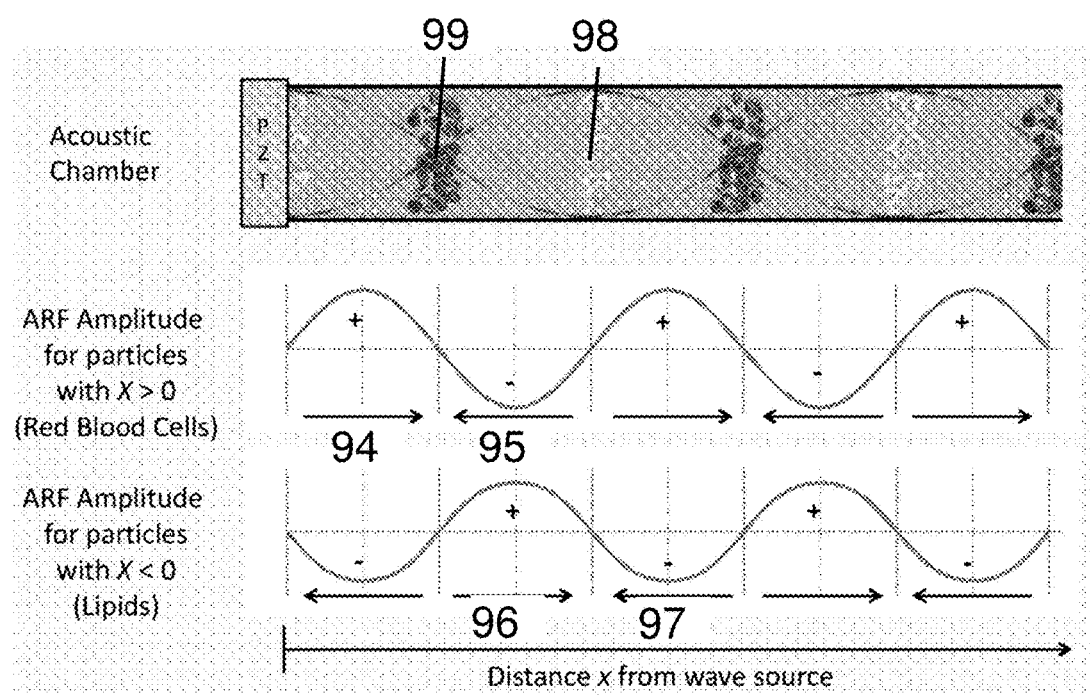
FIG. 9 is a graph showing lipids and blood cells trapped in standing waves.

FIG. 9 shows the acoustic radiation force (ARF) felt by particles having positive and negative acoustic contrast factors. For the red blood cells, having a contrast factor greater than zero, forces 94 and 95 push the blood cells to a node 99 of a standing wave which is a half wavelength from the node 98 where the lipids collect. The lipids are pushed to anti-node 98 by forces 96 and 97. The blood cells and lipids feel different forces because particles having a positive acoustic contrast factor move to the pressure node 99, and particles having a negative acoustic contrast factor move to the pressure anti-node 99. In other words, the lipids are separated from the red blood cells in columns by half a wavelength. The standing waves are generally perpendicular to the flow direction, and the columns will be generally parallel to the flow direction. As the lipids coalesce, they eventually become buoyant and will float to the top. The red blood cells will sink to the bottom, and can either be separately collected or can travel with the remainder of the blood back to the patient.

Figure 10:
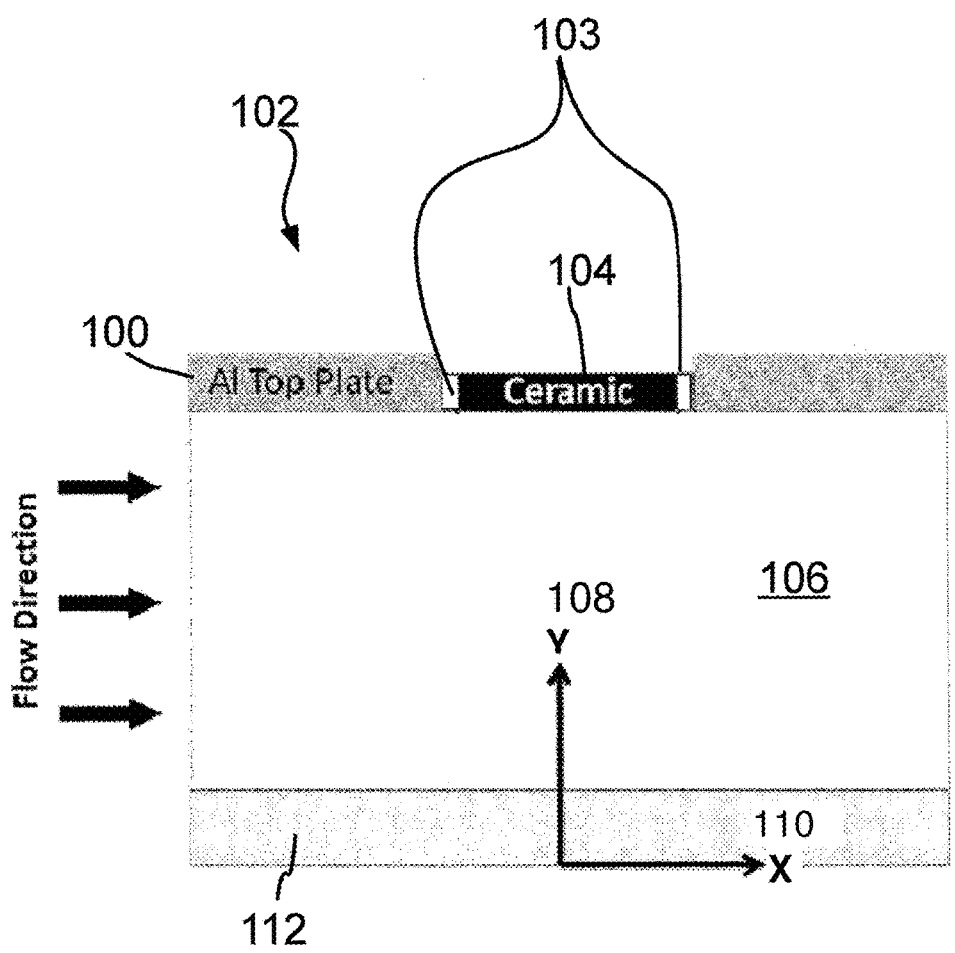
FIG. 10 is a computer model of an acoustophoretic separator simulated to generate FIGS. 11A-D.

FIG. 10 is a computer model of an acoustophoretic separator 102 simulated to produce FIGS. 11A-11D. The piezo ceramic crystal 104 is in direct contact with the fluid in the water channel 106. In an embodiment for separation of lipids from blood, it is anticipated that a thin wear plate would be used. A layer of silicon 103 is between the crystal 104 and the aluminum top plate 100. A reflector 112 reflects the waves to create standing waves. The reflector is made of a high acoustic impedance material such as steel or tungsten, providing good reflection. For reference, the Y-axis 110 will be referred to as the axial direction. The X-axis 108 will be referred to as the radial or lateral direction. The acoustic pressure and velocity models were calculated in COMSOL including piezo-electric models of the PZT transducer, linear elastic models of the surrounding structure (e.g. reflector plate and walls), and a linear acoustic model of the waves in the water column. The acoustic pressure and velocity was exported as data to MATLAB. The radiation force acting on a suspended particle was calculated in MATLAB using Gor'kov's formulation. The particle and fluid material properties, such as density, speed of sound, and particle size, are entered into the program, and used to determine the monopole and dipole scattering contributions. The acoustic radiation force is determined by performing a gradient operation on the field potential U, which is a function of the volume of the particle and the time averaged potential and kinetic energy of the acoustic field.

Figure 11A:
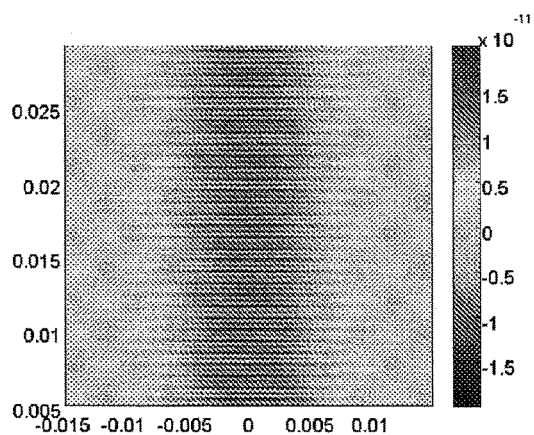
FIGS. 11A-D show simulations of the forces on a particle in an acoustophoretic separator.
Figure 11B:
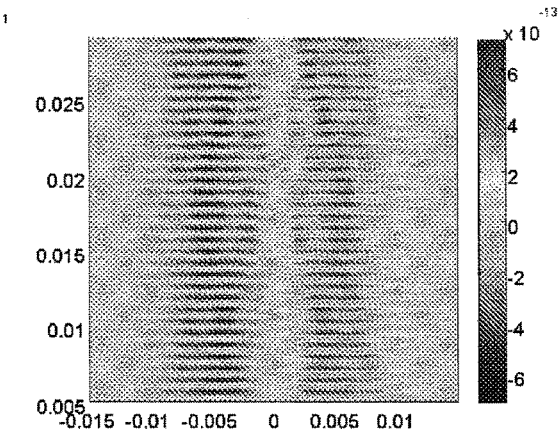
Figure 11C:
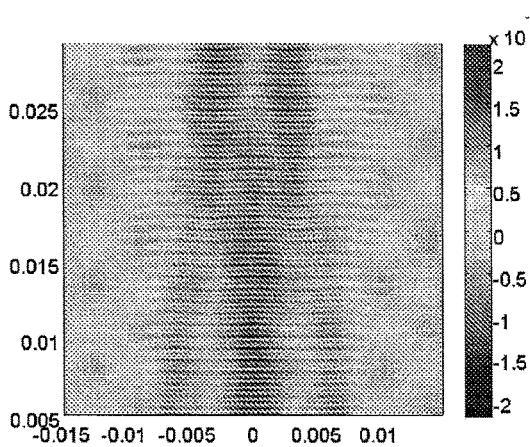
Figure 11D:
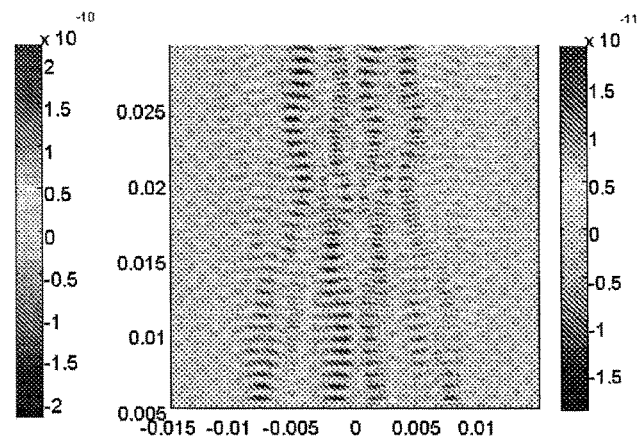

FIGS. 11A-11D show simulations of the difference in trapping between a single acoustic wave and a multimode acoustic wave. FIG. 11A shows the axial force associated with a single standing acoustic wave. FIG. 11B shows the lateral force due to a single standing acoustic wave. FIGS. 11C and 11D show the axial force and lateral force, respectively, in a multi-mode (higher order vibration modes having multiple nodes) piezoelectric crystal excitation where multiple standing waves are formed. The electrical input is the same as the single mode of FIGS. 11A and 11B, but the trapping force (lateral force) is 70 times greater (note the scale to the right in FIG. 11B compared to 11D). The figures were generated by a computer modeling simulation of a 1 MHz piezo-electric transducer driven by 10 V AC potted in an aluminum top plate in an open water channel terminated by a steel reflector (see FIG. 10). The field in FIGS. 11A and 11B is 960 kHz with a peak pressure of 400 kPa. The field in FIGS. 11C and 11D is 961 kHz with a peak pressure of 1400 kPa. In addition to higher forces, the 961 kHz field (FIGS. 11C and 11D) has more gradients and focal spots.

Figure 12:
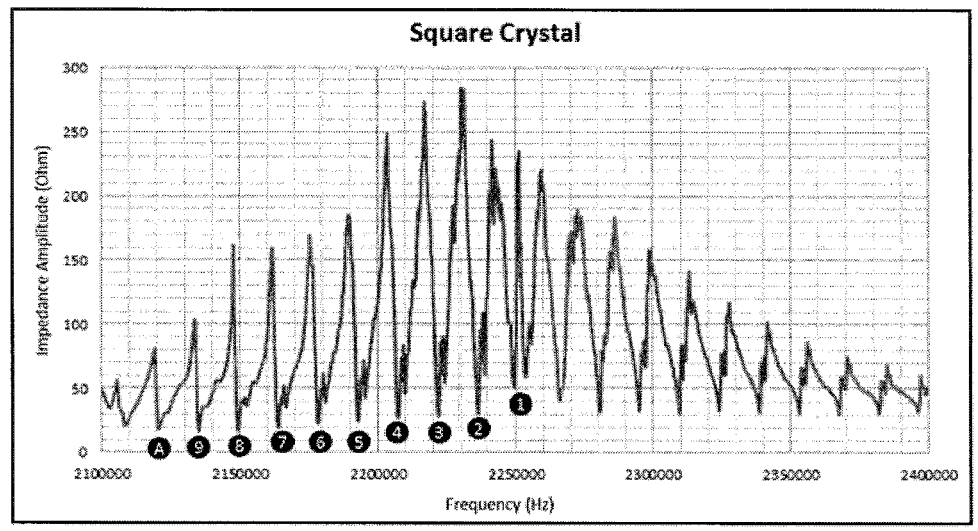
FIG. 12 is a graph of impedance amplitude versus frequency as a square transducer is driven at different frequencies.

In addition to the shape of the transducer, the shape of the mode of the transducer (in what shape the transducer is vibrating) affects oil separation efficiency. Producing more nodes provides more places for oil to be trapped. FIG. 12 shows the measured electrical impedance amplitude of the transducer as a function of frequency in the vicinity of the 2.2 MHz transducer resonance. The minima in the transducer impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. The transducer displacement mode shape varies from a single half wavelength mode to a three half wavelength mode shape. Higher order transducer modal displacement patterns result in higher trapping forces and multiple stable trapping locations for the captured oil droplets. A single half wavelength mode results in one line of trapped droplets, whereas a three half wavelength mode results in three parallel lines of trapped droplets across the fluid channel.

To investigate the effect of transducer mode shape on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 12, were used as excitation frequencies. The conditions were experiment duration of 30 min, a 1000 ppm oil concentration, a flow rate of 500 ml/min, and an applied power of 20 W.

Figure 13:
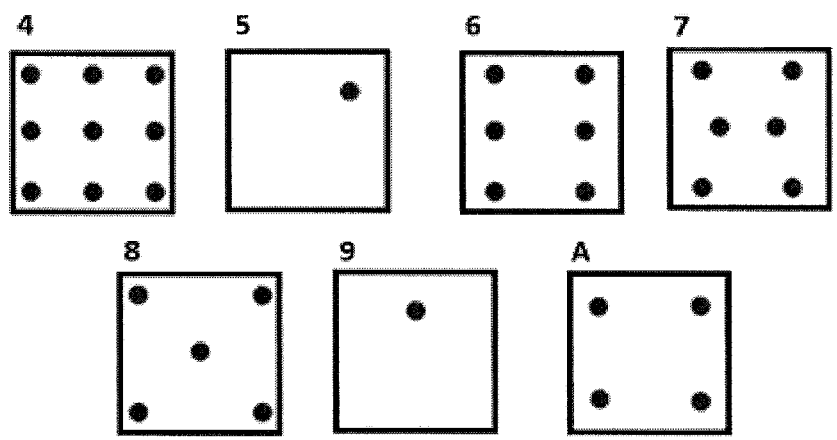
FIG. 13 illustrates the node configurations for seven of the peak amplitudes of FIG. 19.

As the emulsion passed by the transducer, the trapping nodal lines were observed and characterized. The characterization involved the observation and pattern of the number of nodal trapping lines across the fluid channel, as shown in FIG. 13, for seven of the ten resonance frequencies identified in FIG. 12.

The effect of excitation frequency clearly determines the number of nodal trapping lines, which vary from a single trapping line at the excitation frequency of acoustic resonance 5 and 9, to nine trapping nodal lines for acoustic resonance frequency 4. At other excitation frequencies four or five nodal trapping lines are observed. Different modes of vibration of the transducer can produce different (more) nodes of the standing waves, with more nodes generally creating higher trapping forces.

Figure 14:
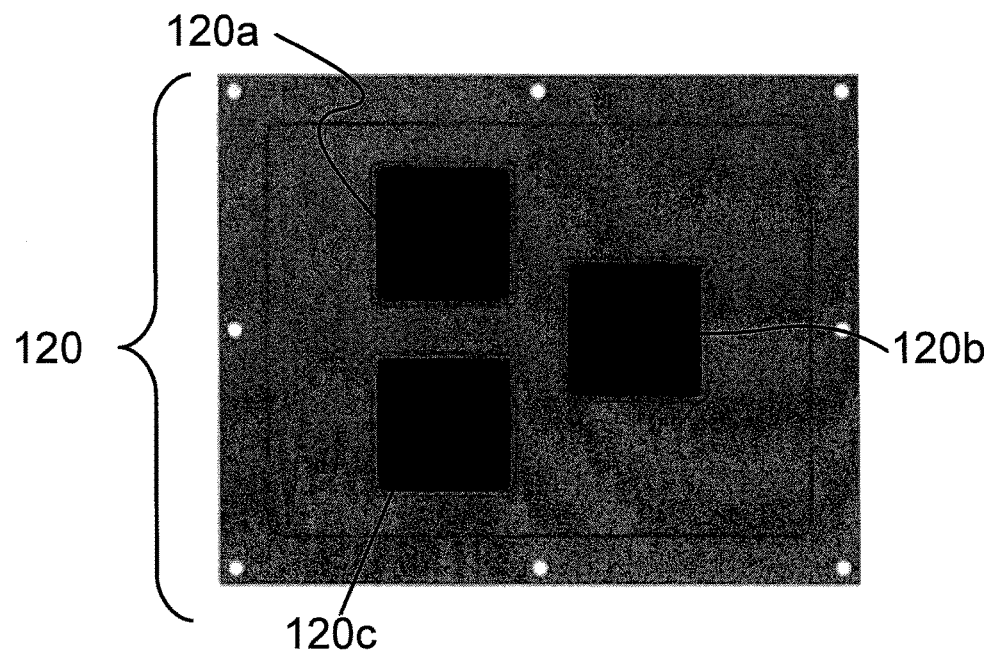
FIGS. 14 and 15 show transducer array configurations.
Figure 15:
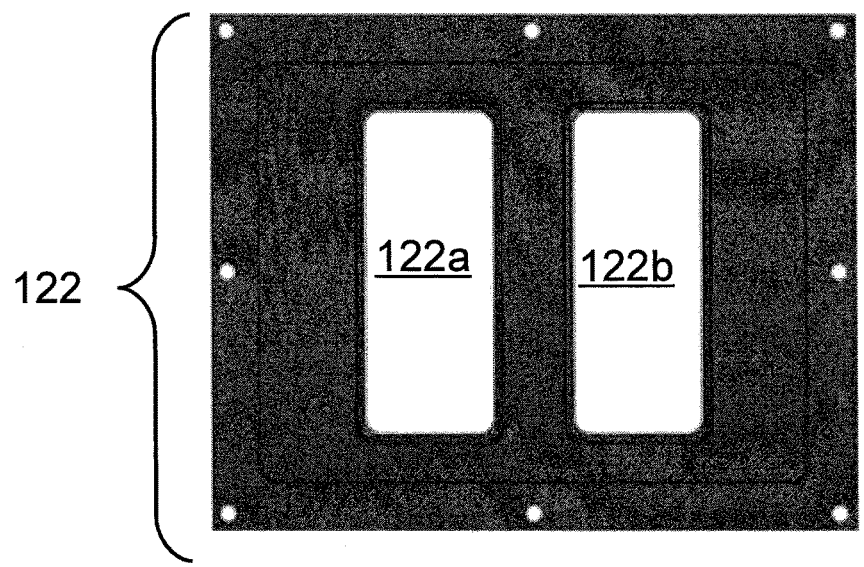

Different transducer arrangements are feasible. FIG. 14 shows a transducer array 120 including three square 1"×1" crystals 120a, 120b, 120c. Two squares are parallel to each other, and the third square is offset to form a triangular pattern. FIG. 15 shows a transducer array 122 including two rectangular 1"×2.5" crystals 122a, 122b arranged with their long axes parallel to each other. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W.

Figure 16:
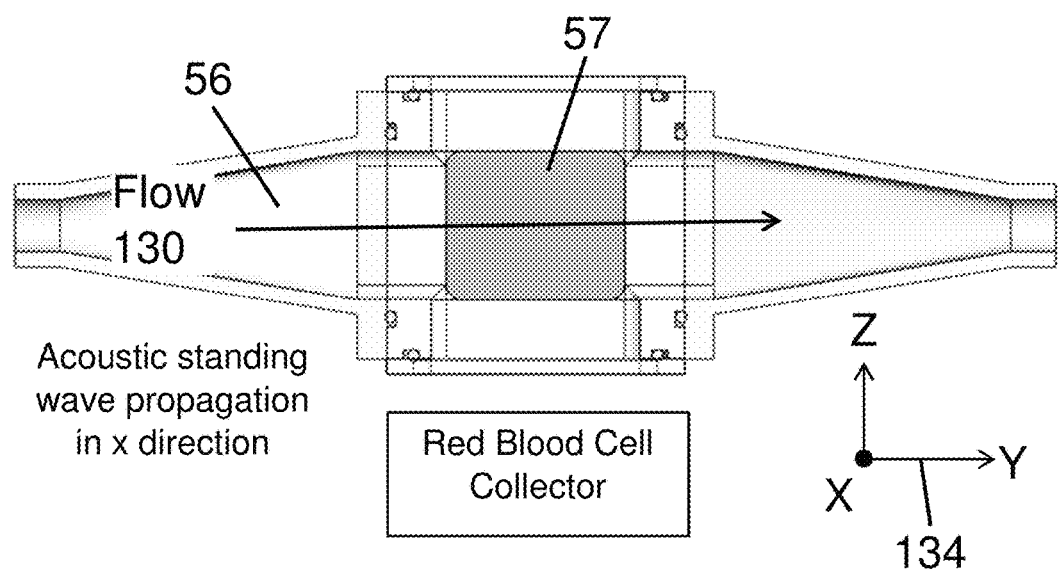
FIG. 16 is a photo of the acoustophoretic separator of FIG. 5 in a lab setup to remove red blood cells.

FIG. 16 shows a lab setup using separator 56 to remove red blood cells from a stream of blood. Flow of the blood is in direction 130. The acoustic propagation of the waves is in the X-direction (coming out of the page in FIG. 16). That is, the photo shows steel plate 57 and the transducer is on the opposite side of separator 56.

A series of tests were performed using the setup of FIG. 16, with bovine blood diluted 100×, 50×, 25×, and 10×. In all four tests, the blood cells could be viewed through separator window 64. Further tests were performed using 10× diluted bovine blood with a 0.75% safflower emulsion. Oil was visually observed rising to the top. Hematocrit readings, a measure of red blood cell concentrations, were taken from the chamber of the separator 56. The time and readings were: 3% at 0 minutes (baseline), 55% at 10 minutes, and 23% at 20 minutes. It is believed that the drop at 20 minutes is due to decreased red blood cell count after the drawing at 10 minutes.

Figure 17:
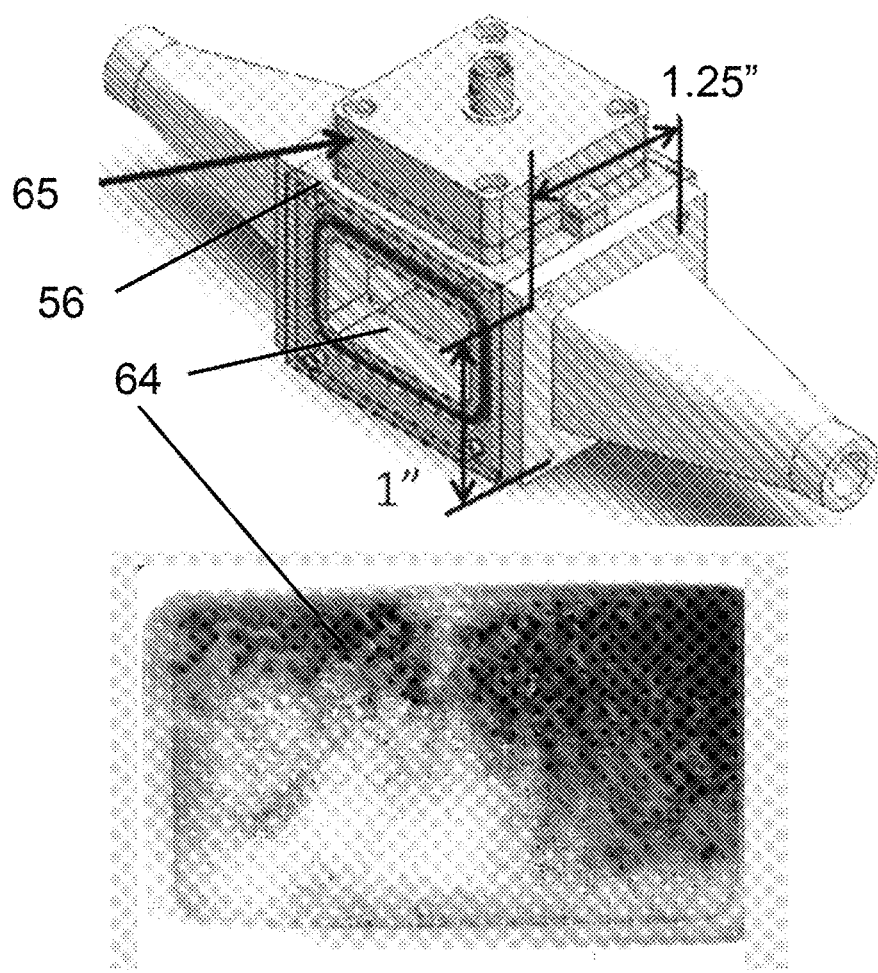
FIG. 17 shows two photos of a viewing window of the acoustophoretic separator of FIG. 5 and FIG. 16.

FIG. 17 shows two pictures of window 64 showing oil agglomerating and rising out of the acoustic standing wave. This demonstrates that acoustophoretic separation is an effective method for concentrating red blood cells and lipid separation to prevent microemboli.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of separating lipids from blood, the method comprising:
   flowing the blood through a flow chamber, wherein the flow chamber has a source of acoustic energy with an initial shape and, on an opposing side of the flow chamber, a reflector of acoustic energy, and wherein the blood contains lipids;
   driving the source of acoustic energy at a frequency that generates a higher order mode shape than the initial shape to create a plurality of three-dimensional standing waves in the blood; and
   removing lipids trapped in the three-dimensional standing waves from the blood;
   wherein each three-dimensional standing wave results in an acoustic radiation force with an axial force component and a lateral force component that are of the same order of magnitude.

2. The method of claim 1, wherein the blood is continuously flowed through the flow chamber.

3. The method of claim 1, wherein the standing waves create nodal lines and the lateral forces trap the lipids in the nodal lines.

4. The method of claim 3, wherein the lipids trapped in the nodal lines coalesce or agglomerate such that the lipids are separated through enhanced buoyancy.

5. The method of claim 1, wherein the lipids are collected in a collection pocket at the top of the flow chamber.

6. The method of claim 1, wherein the blood is mediastinal blood collected via a suction.

7. The method of claim 1, wherein the source of acoustic energy is an ultrasonic transducer comprising:
   a housing with a top end, a bottom end, and an interior volume; and
   a crystal at the bottom end of the housing with an exposed exterior surface and an interior surface, the crystal being able to vibrate when driven by a voltage signal; and
   an air gap between the crystal and the top end of the housing.

8. A method of separating lipids from blood, the method comprising:
   flowing the blood through a flow chamber, wherein the flow chamber has a source of acoustic energy with an initial shape and, on an opposing side of the flow chamber, a reflector of acoustic energy, and wherein the blood contains lipids;
   driving the source of acoustic energy at a frequency that generates a higher order mode shape than the initial shape to create a plurality of three-dimensional standing waves in the blood; and
   removing lipids trapped in the three-dimensional standing waves from the blood;
   wherein each three-dimensional standing wave results in an acoustic radiation force with an axial force component and a lateral force component that are of the same order of magnitude; and
   wherein the source of acoustic energy is an ultrasonic transducer comprising:
   a housing with a top end, a bottom end, and an interior volume; and
   a crystal at the bottom end of the housing with an exposed exterior surface and an interior surface, the crystal being able to vibrate when driven by a voltage signal, wherein a backing layer contacts the interior surface of the crystal, the backing layer being made of a substantially acoustically transparent material.

9. The method of claim 8, wherein the substantially acoustically transparent material is balsa wood, cork, or foam.

10. The method of claim 8, wherein the substantially acoustically transparent material has a thickness of up to 1 inch.

11. The method of claim 8, wherein the substantially acoustically transparent material is in the form of a lattice.

12. The method of claim 7, wherein an exterior surface of the crystal is covered by a wear surface material with a thickness of a half wavelength or less, the wear surface material being a urethane, epoxy, or silicone coating.

13. The method of claim 7, wherein the crystal has no backing layer or wear layer.

14. The method of claim 7, further comprising driving the crystal in a non-uniform displacement mode.

15. The method of claim 14, further comprising driving the crystal in a higher order mode shape to produce more than one nodal trapping line.

* * * * *